United States Patent
Dell'Acqua

(10) Patent No.: US 10,610,541 B2
(45) Date of Patent: Apr. 7, 2020

(54) PREBIOTICS

(71) Applicant: VANTAGE SPECIALTIES, INC., Warren, NJ (US)

(72) Inventor: Giorgio Dell'Acqua, Jersey City, NJ (US)

(73) Assignee: VANTAGE SPECIALTIES, INC., Warren, NJ (US)

(*) Notice: Subject to any disclaimer, the term of this patent is extended or adjusted under 35 U.S.C. 154(b) by 0 days.

(21) Appl. No.: 15/941,012

(22) Filed: Mar. 30, 2018

(65) Prior Publication Data

US 2018/0280424 A1   Oct. 4, 2018

Related U.S. Application Data

(60) Provisional application No. 62/479,862, filed on Mar. 31, 2017.

(51) Int. Cl.
 *A61K 31/716* (2006.01)
 *A61K 9/50* (2006.01)
 *A61K 9/00* (2006.01)

(52) U.S. Cl.
 CPC .......... *A61K 31/716* (2013.01); *A61K 9/0014* (2013.01); *A61K 9/5015* (2013.01); *A61K 9/5047* (2013.01)

(58) Field of Classification Search
 CPC .................................................... A61K 31/716
 See application file for complete search history.

(56) References Cited

U.S. PATENT DOCUMENTS

| 9,084,434 | B2* | 7/2015 | Hodal, Jr. | A61K 9/2018 |
| 9,271,924 | B2 | 3/2016 | Lanzalaco et al. | |
| 2005/0266069 | A1* | 12/2005 | Simmons | A61K 9/1617 424/451 |
| 2006/0210524 | A1* | 9/2006 | Mower | A61K 8/29 424/74 |

OTHER PUBLICATIONS

Rokka et al (Eur Food Res Technol (2010) 231:1-12) (Year: 2010).*

* cited by examiner

*Primary Examiner* — Benjamin J Packard
(74) *Attorney, Agent, or Firm* — Fox Rothschild LLP

(57) ABSTRACT

A composition which comprises a prebiotic or a mixture thereof that, upon application to an individual's skin, has a beneficial effect on the skin and that is incorporated in the composition in the form of a multiplicity of tiny beads which comprise, in addition to the prebiotic, a matrix-forming agent, for example, mannitol and hydroxypropyl methylcellulose, and a filler, for example, microcrystalline cellulose, and a personal care composition which includes the beads.

20 Claims, No Drawings

PREBIOTICS

CROSS-REFERENCE TO RELATED APPLICATION

This application claims the priority benefit of U.S. provisional Application No. 62/479,862 filed Mar. 31, 2017, the entirety of which is incorporated herein by reference.

FIELD OF THE INVENTION

The present invention relates to the preparation of compositions which comprise prebiotics. More particularly, the present invention comprises the use of prebiotics in applications involving the treatment of skin.

Prebiotics are materials which are to be distinguished from materials known as "probiotics" whose characterization and bodily functions were recognized by the scientific community at a time prior to recognition by scientists of the nature and bodily functions of prebiotics.

Speaking generally, the aforementioned, previously recognized probiotics are live bacteria that perform valued bodily functions in the intestinal tract of humans. Sources of probiotics are foods and dietary supplements, which are ingested by individuals, for example, dairy products such as yogurt, and dietary supplements in the form of pills that include one or more desirably effective breeds of bacterial strains.

On the other hand, prebiotics can be characterized in simple and general terms as a "fertilizer" for probiotics in that they enhance and promote the growth of desirable bacterial strains of probiotics, including particularly those which otherwise tend to be degraded or killed in the stomach before they reach the intestinal tract. In one sense, prebiotics can function as protectors of various types of probiotics which would otherwise die off before performing desirable bodily functions.

Prebiotics are typically carbohydrate-based polymers. Examples of materials which comprise prebiotics are in general plant fibers that are present in vegetables and fruits that can be ingested directly and/or taken in the form of dietary supplements. Examples of foods that are sources of prebiotics include dry raw forms of leeks, artichokes, garlic, chicory root, and onion. Dietary supplements can include, for example, such foods and apple skin.

Scientific research to date has concentrated mainly on the nature of bodily functions performed by probiotics and prebiotics in the gut. More recently, the scientific community has begun to consider the use of applications of probiotics and prebiotics in the treatment of skin, including, for example, facial skin. There are significant groups of individuals whose facial skin suffers from afflictions which are painful and/or unsightly. Examples of afflictions which can be both painful and unsightly include sensitive, dry, cracked skin, acne, and eczema. Examples of unsightly afflictions include redness and slight swelling.

A challenge which confronts the scientific community is to determine whether or not the useful bodily functions which are performed in the gut by the presence of the combination of probiotics and prebiotics can be harnessed in a manner such that the topical applications of the combination to an individual's skin functions to maintain and/or improve the quality of the skin.

SUMMARY OF THE INVENTION

In one respect, the present invention provides a delivery system for applying to the outer surface of the skin of an individual one or more prebiotics in which the prebiotic(s) is encapsulated in a multiplicity of tiny beads. Still another aspect of the present invention is the provision of a composition in which the prebiotic(s) is encapsulated comprises a soft flowable texture.

In another aspect, the present invention provides a composition in the form of a plurality of spherical beads having a diameter within the range of about 425 to about 1000 microns, and in which the composition of the beads comprises: (A) one or more prebiotics that upon application to the skin's surface has a beneficial effect on the skin; (B) a filler, preferably microcrystalline cellulose; and (C) a matrix-forming agent having a soft flowable texture which permits the beads to be spread readily on the skin's surface and to which the beads are capable of adhering for a period at least as long as it takes for the prebiotic(s) to perform its function, said agent comprising preferably a mixture of mannitol and hydroxypropyl methylcellulose.

With respect to the above composition, the various ingredients which are bound together with the prebiotic can function in multiple ways to form a highly effective delivery bead. For example, the ingredients include materials which function as adhesives and softening agents. The hydroxypropyl methylcellulose binds the ingredients together in shape-retaining form and the mannitol allows the beads to soften when in contact with water, for example, during use.

As will be appreciated from the detailed description of the invention as set forth below, the present bead delivery system for the prebiotic provides an efficient and effective way to condition the skin's surface and to normalize the skin's microbiome in a natural and healthy way while at the same time stimulating the skin's defenses. The overall result is the creation of an environment that prevents or curtails opportunities for invasions of the skin by undesirable bacteria. Stressed skin is weakened. Soothing and improving the skin's barrier and microbiome balance lead to a healthier, glowing, and beautiful skin. The encapsulation of the prebiotics facilitates their utilization and ensures stability of the formulation and its delivery.

Introductory Background Information

An individual's skin is home to trillions of bacteria (both good & bad) which form a layer that is referred to as "skin flora" or "skin microbiota". Examples of normal skin flora are *staphylococcus epidermidis; staphylococcus aureus; streptococcus* sp.; *corynebacteria* sp.; *micrococcus* sp.; *bacillus* sp.; *peptrostrepoccus* sp.; *neisseria* sp.; *propionibacterium* sp.; *diptheroids; candida* sp.; *acinetobacter* sp.; and *mycobacterium* sp. The aforementioned layer is one of many first line defenses against the development of "skin" afflictions which have an adverse effect on the natural beauty of the skin, particularly facial skin. The afflictions are described briefly above; they are described comprehensively hereinafter along with objective tests which can be used to evaluate the efficiency of treatments that are used to improve the properties of skin.

Different strains of bacteria function in different ways. The "good" bacteria comprise an ecosystem which is essential for helping to maintain the skin in proper condition. The "good" bacteria are classified as either transient or resident and are considered to be beneficial or essentially neutral. Other bacteria are pathogenic or at least have the capacity to be pathogenic and to affect adversely the condition of the skin. On average, an individual's skin has 100 times more bacterial cells than human cells. In effect, the skin of an individual is more microbial than it is human.

In accordance with the present invention, means are provided for the good bacteria to curtail or prevent the colonization of bad bacteria in order to ward off infections and other skin diseases. This is particularly important for individuals who have dry or cracked skin, or where the skin's acid mantel and/or lipid barriers are compromised as infection and other diseases invade the skin.

DETAILED DESCRIPTION OF THE INVENTION

Prebiotics for use in the practice of the present invention are those that upon application to the skin's surface have a beneficial effect on the skin. There is described hereinafter tests which are used to evaluate objectively whether a particular treatment of the skin has a beneficial effect, a neutral effect, or an adverse effect.

The discussion which follows immediately identifies three materials which are recommended prebiotics for use in the present invention. They are referred to hereinafter as: (A) fucoidan; (B) beta-glucan; and (C) inulin.

Fucoidan is a sulfated, fucose-rich polysaccharide which has an average molecular weight of about 20,000. It exhibits potentially beneficial bioactive functions in humans. For example, it assists with protection from marine pathogens and it has shown anti-viral, immune modulating and matrix metalloprotease-inhibiting properties in the skin. It can help to smooth and regenerate the skin and also to stimulate skin defenses.

There are various sources of fucoidan. For example, it is found mainly in various species of brown algae, for example, kelp and of seaweeds, for example, mozku; komu; bladderwrack; wakame; and hijki. The art recognizes that there are at least two distinct forms of fucoidan, namely F-fucoidan which comprises in excess of about 95% of sulfated esters of fucose and U-fucoidan which comprises about 20% glucuronic acid.

A recommended fucoidan for use in the practice of the present invention is wakame seaweed (undaria pinnatifida), for example, purified to about 85 wt. %.

Beta-glucans for use in the practice of the invention can function in various ways. They can balance the microflora and they can function by activating Langerhans cells and keratinocytes signaling pathways. The Langerhans cells improve the over-all health and youthful appearance of the skin by stimulating an immune defense. In addition, they help to protect the skin from major infections and provide means to help repair the day-to-day wear to which the skin is exposed.

Beta-glucans are high-molecular weight polysaccharides, sources of which are plant and animals. They are present as a natural component of the cell walls of bacteria, fungi, yeast, and cereals, for example, oat and barley. Examples of fungi which are sources of beta-glucan are antrodia; cordyceps; coriolus; maitake; reishi; pleurotus; shitake; and suchirotake. Other sources of beta-glucans are: algae; gram negative bacteria; and brown seaweeds.

For use in the present invention, it is particularly recommended that the beta-glucan be derived from a yeast cell wall and purified to about 90%. It is characterized by a 1,3/1,6 linkage structure and is water insoluble. This configuration of the beta-glucan makes it particularly potent in stimulating skin immunity.

Inulin is a storage carbohydrate found in many plants. It is naturally found in vegetables and fruits as well as cereals. After starch, inulin is the most abundant non-structural polysaccharide found in nature. It is a polydispersed carbohydrate material consisting mainly of B(2>1) fructosyl-fructose links. A recommended inulin is 98% pure and extracted from the roots of the chicory plant (*cichorium intybus*). It is highly branched and this conformation makes it water insoluble.

Other examples of sources of inulin are: sprouted wheat; shallots; artichokes; rye; leaks; dandelion root; asparagus; onions; bananas and plantains; garlic; yams; burdock root; coneflower jicama; and yacon root.

The following are additional examples of prebiotics for use in the practice of the present inventions: levan, kefiran, fructan, mucopolysaccharides, oligosaccharides, polysaccharides, galactooligosaccharide, hydroxyisoleucine, wheat dextrin, arabinogalactan, citrus fiber, pea fiber, maltodextrin, fructooligosaccharides, inulin oligofiber, pectin, resistant starch, mannan hydrolysates, glucomannan hydrolysates, galactomannan, gentiooligosaccharides, isomaltooligosaccharide, xylooligosaccharides, transgalactooligosaccarides, polydextrose, acacia gum, whole grain wheat, whole grain corn, lactulose, oligofructose, ulvan, mutan, reuteran, alternan, and lactilol.

For various reasons, the amount of prebiotic included in the beads hereof can vary over a wide range. For example, prebiotics can themselves vary widely in their chemical makeup. Consideration needs to be given also to the other ingredients comprising the bead and to the nature of the affliction which is to be treated by the use of the prebiotics. Also, the particular form in which the beads are applied to the skin needs to be taken into account.

In view of the aforementioned, consider the following "amount" information as guidelines for selecting amounts for any particular application.

In addition to the prebiotic and, as stated above, the delivery beads of the present invention contain other ingredients which make them suitable for use as a delivery agent, including a matrix-forming agent (softening agent and adhesive), and filler, for example, in appropriate amounts within the following ranges:

(A) about 0.0001 to about 50 wt. % of prebiotic(s);
(B) about 30 to about 75 wt. % of a matrix-forming agent; and
(C) about 15 to about 45 wt. % of filler.

An additional example of amount ranges of ingredients that can be included in the composition of the present invention is set forth below:

(A) about 0.0001 to about 50 wt. % of prebiotic(s);
(B) about 30 to about 65 wt. % of softening agent;
(C) about 0.5 to about 10 wt. % of adhesive; and
(D) about 15 to about 45 wt. % of a filler.

The bead can include also optional ingredients for imparting desired properties to the beads, for example, pigments and other ingredients such as, for example, anti-oxidants, oils, silicas, and water insoluble materials. Optional ingredients can comprise up to about 50 wt. % of the bead.

A preferred bead comprises:

(A) about 1 to about 50 wt. % of prebiotic(s);
(B) about 30 to about 65 wt. % of mannitol;
(C) about 0.5 to about 10 wt. % of hydroxypropylmethylcellulose; and
(D) about 15 to about 45 wt. % of microcrystalline cellulose.

It is noted that ingredients (C) and (D) above are themselves considered to have prebiotic properties.

In preferred form, a composition of the present invention is free of or substantially free of a probiotic, that is, the composition contains no more than about 0.1 wt. % of a probiotic based on the total weight of the composition.

An example of a process for preparing the beads includes the following steps: (A) mixing of raw materials (dry blend); (B) wet granulation; (C) extrusion to pellets; (D) spheronizing to round beads; (E) drying in oven; and (F) sieving to narrow sizes.

The beads possess a combination of properties which make them suitable for combining with other ingredients to form a variety of formulations suitable for use as personal care compositions including, for example, skin-care compositions which can be applied readily to the skin of an individual. Examples of such formulations include cosmetic formulations, liquid soaps, shower gels, body washes, and shampoo. Examples of ingredients of such formulations include thickeners, viscosity modifiers, emollients, emulsifiers, and surfactants. The beads can be used, for example, in heavy or semi-solid creams or viscous solutions which are in the form of emulsions and hydrogels. Examples of ingredients that can be included in such formulations are biopolymers, for example, hyaluronic acid, xanthan gum, synthetic thickeners (CARBOPOL®), and cellulose ethers. It is recommended that the formulations have a minimum content of about 15 wt. % water to aid in the softening of the beads. Exemplary concentrations of the beads in such formulations are within the range of about 0.5 to about 3 wt. %. The use of thickeners helps the beads to stay suspended in the formulation.

After the formulation is applied on the skin, mechanical pressure (rub out) with the fingers will break and dissolve the beads that will release their content in the formulation and on the skin. The formulation containing the dissolved beads will then be absorbed by the skin providing the benefits sought.

The following includes a description of the properties of the beads and of various characteristics of the beads. The beads are not soluble in water. When added to formulations containing water, like emulsions, surfactant products, or aqueous gels, water will penetrate the beads and soften them; this may take some hours, depending on the type and the composition of the final product. In pure water, they will soften within a few minutes. In cosmetic formulations with a small amount of free, non-bonded water, this process can take some hours to some days. Increasing temperatures accelerate the softening process. As the beads are macroscopic solid pellets, any mechanical influences should be avoided during manufacturing and filling procedures. Homogenizing a cosmetic formulation through intensive stirring is a risk to destroying mechanically the beads. The beads should be added at the end of the manufacturing process only with slow stirring. For storage and filling, the bulk product can be safely pumped (using a membrane, peristaltic or piston pump) and filled without breakage. It is recommended that filling cosmetic products be done as soon as possible after the addition of the beads, while they are still hard, as the risk of breaking will increase with the softening of the beads.

In all water-containing finished products, cellulose beads are stable in a wide range of pH (4-8). Between −5° C. and +50° C., no instabilities of shape or structure have been observed. At those temperatures, all basic components do not melt or decompose.

Only when added to a formulation, some physical effects must be considered: freezing of a formulation, as it is used for stability testing, may lead to the formation of ice crystals inside the beads, which destroy the structure of the beads; and elevated temperatures during processing will significantly accelerate the softening of the beads.

There follows a discussion of the immunological barrier of the skin and its relationship to skin microbiome. As stated above, the skin represents not only a physical barrier but also an immunological one. The composition of the microbiome is influenced by the host's native and adaptive immune systems.

A critical function of the epidermis is the cutaneous skin's innate immune system which orchestrates when and how the immune system should respond to normal or pathogenic microbes depending on their species, number, or location on the body. The epidermis, which directly borders with the environment, expresses a variety of receptors, peptides, lipids, and signaling molecules that, in tandem, signal downstream processes that control the function of the skin in terms of barrier, differentiation, thickness, lipid production, and pH. In addition, these processes include and are complexed with key aspects of the innate immune surveillance system.

Thus, the cutaneous innate immune system can be viewed as a key determinant of the immunologic barrier functions of the epidermis. Malfunctions in this system can lead to an imbalance in skin homeostasis and an inappropriate skin response to a pathogen and persistent inflammation. Key drivers, also referred to as "targets", represent these pathways and processes are listed in attached Appendix A. These targets are key to monitoring the effects of a healthy or unhealthy skin microbiome or skin ecology and can be used as diagnostic indicators of skin health and the effects of prebiotic function.

It is stated above that there are "skin" afflictions which have an adverse effect on the natural beauty of the skin and that there are tests which are used objectively to evaluate whether a particular treatment of the skin has a beneficial, neutral, or adverse effect on the skin. There are described below various skin afflictions, how they develop, and means used to evaluate objectively the degree or severity of the affliction. Such afflictions include, for example, atopic dermatitis and/or atopic dry skin or xerosis, acne, photoaged skin, skin hydration, and skin damage induced by UV radiation.

Evaporation of water from the skin occurs always as a part of the normal skin metabolism. As soon as the barrier function of the skin, however, is slightly damaged, the water loss will increase (even with smallest damages invisible to the human eye). Therefore, this measurement is a basis for all cosmetic and dermatological research. The Tewameter probe measures the density gradient of the water evaporation from the skin indirectly by the two pairs of sensors (temperature and relative humidity) inside a hollow cylinder. This is an open chamber measurement. The open chamber measurement method is the only method to assess the trans epidermal water loss (TEWL) continuously without influencing its micro environment. A microprocessor analyses the values and expresses the evaporation rate in $g/h/m^2$.

Measurement of skin hydration is based on capacitance measurement of dielectric medium. The Corneometer measures the change in the dielectric constant due to skin surface hydration changing the capacitance of a precision capacitor. The measurement can detect even slight changes in the hydration level.

The topography of the skin surface is a polygonal microrelief with furrows and wrinkles representing the three-dimensional organization of the epidermis, dermis, and the subcutaneous tissue. It depends on morphological characteristics like thickness of the cornified layer and collagen content, and it may be considered as a mirror of the functional status of the skin. The quantitative determination of the skin's surface topology, both skin roughness and macrostructures, such as wrinkles, is one of the most important and frequently performed non-invasive clinical investigations. The skin's microrelief will alter progressively with age, including the appearance of wrinkles. Changes to the surface profile of the skin caused by formation of fine lines and wrinkles increase with age primarily as a result of UV-exposure. Non-invasive instrumental measurement is based on a series of devices. Wrinkles can be measured using the Fringe Projection method to measure, in 3-D, the depth and breadth of wrinkles and fine lines and/or using quality standardized high-resolution digital photography.

EXAMPLES

The following is a description of the preparation of prebiotic beads of the present invention and the use of the beads in a "skin" application. The powdery ingredients and amounts comprising the beads are identified below.

The powdery ingredients are mixed in a container using a turbine blade and a spatula. Distilled water is added to the resulting blend until the blend is wet thoroughly utilizing a pipette in a process known as "wet granulation". The wet blend is extruded using a 0.6 mm screen. The wet beads are formed into a spherical shape by a spheronizer. The spherically shaped wet beads are placed in a metal tray and dried overnight in an oven having a temperature of 40° C. Thereafter, the dried beads are sieved through a 425-1000 micron screen. Spherical beads having a diameter of about 425 to about 1000 microns are recovered.

Following the above procedure, four batches of beads were prepared from four different compositions, which are described below. Each batch of beads weighed 500 grams; the "%" of ingredients comprising the beads is "wt. %".

Bead 1—ingredients:

| Mannitol | 291 grams | (58.2%); |
| microcrystalline cellulose | 179 grams | (35.8%); |
| hydroxypropyl methylcellulose | 25 grams | (5%); |
| yeast beta glucan | 5 grams | (1%); | distilled water added-180 milliliters per preparation of wet blend

Bead 2—ingredients:

| Mannitol | 291 grams | (58.2%); |
| microcrystalline cellulose | 179 grams | (35.8%); |
| hydroxypropyl methylcellulose | 25 grams | (5%); |
| Fucoidan | 5 grams | (1%); | distilled water added-180-milliliters per preparation of wet blend.

Bead 3—ingredients:

| Mannitol | 264.54 grams | (52.91%); |
| microcrystalline cellulose | 162.73 grams | (32.55%); |
| hydroxypropyl methylcellulose | 22.73 grams | (4.54%); |
| Inulin | 50 grams | (10%); | distilled water added-120 milliliters per preparation of wet blend.

Bead 4—ingredients:

| Mannitol | 258.67 grams | (51.74%); |
| microcrystalline cellulose | 159.11 grams | (31.82%); |
| hydroxypropyl methylcellulose | 22.22 grams | (4.44%); |
| Inulin | 50 grams | (10%); |
| yeast beta glucan | 5 grams | (1%); |
| Fucoidan | 5 grams | (1%); | distilled water added-180 milliliters per preparation of wet blend.

All beads are white/brown in color. Other properties are described in the Table below.

| Ex. No. | Moisture Content, wt. % | Bulk Density, kg/m³ |
|---|---|---|
| Bead 1 | 0.53 | 700 |
| Bead 2 | 0.70 | 810 |
| Bead 3 | 0.85 | 800 |
| Bead 4 | 1.58 | 700 |

The next example is illustrative of a formulation that comprises micro beads in a moisturizing face cream that is non-oily. In use, the face cream improves the overall condition of the skin of the face.

Encapsulated micro beads of the present invention are used in preparing the formulation which includes also other ingredients as described in the procedure set forth below. The encapsulated beads contain the following ingredients in the weight percentages indicated based on the total weight of the beads.

(a) prebiotics: (1) inulin (10%); (2) yeast beta glucan (1%); and (3) undaria pinnatifida extract (1%);
(b) mannitol (51.74%);
(c) microcrystalline cellulose (31.82%); and
(d) hydroxypropylmethyl cellulose (4.44%).

The formulation was prepared in a main vessel by stirring initially 81.4% deionized water (carrier) with 0.1% ethylenediaminetetraacetic acid (chelating agent) with a medium speed propeller. During the stirring, the mixture was heated to 80° C. Thereafter, 0.15% of an acrylates/C10-30 alkyl acrylate cross-polymer was added slowly to the aforementioned heated aqueous mixture using medium to high speed stirring until the cross-polymer was dispersed fully. The cross-polymer functioned as a rheology modifier and is sold under the trademark PEMULEN TR-1 by Lubrizol. Thereafter, 3% glycerin (humectant) was added to the vessel with stirring using a medium speed propeller. In a side vessel, an emulsifier which comprised 6% of the formulation and an emollient blend which comprised 8% of the formulation were mixed together with heating. (The emulsifier and emollient are sold respectively under the trademarks LIPOMULSE LUXE and LIPOVOL MOS-130 by Vantage Specialty Ingredients, Inc.) As the emulsifier and emollient blend were mixed, the mixture was heated to 80° C. and then added to the ingredients in the main vessel as all ingredients were mixed. As the resulting mixture was allowed to cool, 0.35% of a neutralizing agent, an aqueous solution of sodium hydroxide (18 wt. %), was added to the resulting mixture which thickened slightly; it was mixed until a homogeneous mixture was obtained. When the temperature of the ingredients in the main vessel reached 25° to 30° C., 1% of the aforementioned encapsulated beads was added to the ingredients in the main vessel. A preservative (Vantage (Lipo Technologies)—less than about 1%—was added to the resulting formulation which was mixed until it was homogeneous. The formulation has a pH of 6.75 and a viscosity of about 200,000 cps (TF, 1.5 rpm); the formulation was stable for at least about a month at 50° C. The term "%" as used above in describing the proportion of ingredients comprising the formulation means—weight percent—based on the total weight of the ingredients comprising the formulation.

The formulation in the form of a cream can be applied conveniently to the face of an individual until absorbed. During the process of application, the mechanical pressure applied by the fingers in rubbing the cream on the skin of the face breaks the beads in the cream and allows the content of the bead (and the bead itself) to be dispersed and settle on the skin uniformly.

The invention claimed is:

1. A composition consisting essentially of: (A) a prebiotic or a mixture thereof; and (B) one or more other ingredients that function to render the composition suitable for use as a delivery agent to the skin of an individual; and that, upon application to the individual's skin, has a beneficial effect on the skin; said prebiotic being incorporated in the composition in the form of a multiplicity of tiny beads having a diameter within the range of about 425 to about 1000 microns.

2. A composition according to claim 1 including a matrix-forming agent.

3. A composition according to claim 1 including a filler.

4. A composition according to claim 1 including spherical beads.

5. A composition according to claim 3 including a matrix-forming agent having a soft flowable texture which functions to permit the beads to be spread readily on the skin's surface.

6. A composition according to claim 1 comprising:
   (A) about 0.0001 to about 50 wt. % of prebiotic(s);
   (B) about 30 to about 75 wt. % of a matrix-forming agent; and
   (C) about 15 to about 45 wt. % of filler.

7. A composition according to claim 1 comprising:
   (A) about 0.0001 to about 50 wt. % of prebiotic(s);
   (B) about 30 to about 65 wt. % of softening agent;
   (C) about 0.5 to about 10 wt. % of adhesive; and
   (D) about 15 to about 45 wt. % of a filler.

8. A composition according to claim 1 comprising:
   (A) about 1 to about 50 wt. % of prebiotic(s);
   (B) about 30 to about 65 wt. % of mannitol;
   (C) about 0.5 to about 10 wt. % of hydroxypropyl methylcellulose; and
   (D) about 15 to about 45 wt. % of microcrystalline cellulose.

9. A composition according to claim 6 in the form of spherical beads having a diameter within the range of about 425 to about 1000 microns.

10. A composition according to claim 7 in the form of spherical beads having a diameter within the range of about 425 to about 1000 microns.

11. A composition according to claim 8 in the form of spherical beads having a diameter within the range of about 425 to about 1000 microns.

12. An aqueous composition according to claim 1 including at least about 15 wt. % water and about 0.5 to about 3 wt. % of said beads which are not soluble in the water.

13. A method for forming a multiplicity of micro beads having a diameter within the range of about 425 to about 1000 microns comprising forming a mixture of powdery ingredients comprising: (A) a prebiotic; (B) a matrix-forming agent; and (C) a filler; adding to said mixture water and forming therefrom a wet blend of the ingredients; forming the wet blend of ingredients into spherically shaped wet beads, and recovering said micro beads after drying said wet beads.

14. A composition comprising at least about 15 wt. % water, about 0.5 to about 3 wt. % of beads according to claim 1, and ingredients which are effective for use in a personal care composition, said personal care composition being in the form of a cosmetic, liquid soap, shower gel, body wash, shampoo, or moisturizing face cream.

15. A composition according to claim 1 in which the beads are not soluble in water.

16. A composition according to claim 1 wherein the composition contains no more than about 0.1 wt. % of a probiotic.

17. A composition according to claim 1 which is free of a probiotic.

18. A composition according to claim 14 in which the beads are spherical and comprise:
   (A) about 0.0001 to about 50 wt. % of said prebiotic(s);
   (B) about 30 to about 75 wt. % of a matrix-forming agent; and
   (C) about 15 to about 45 wt. % of said filler.

19. A composition according to claim 14 in which the beads are spherical and comprise:
   (A) about 0.0001 to about 50 wt. % of said prebiotic(s);
   (B) about 30 to about 65 wt. % of a softening agent;
   (C) about 0.5 to about 10 wt. % of an adhesive; and
   (D) about 15 to about 45 wt. % of a filler.

20. A composition according to claim 14 in which the beads are spherical and comprise:
   (A) about 1 to about 50 wt. % of said prebiotic(s);
   (B) about 30 to about 65 wt. % of mannitol;
   (C) about 0.5 to about 10 wt. % of hydroxypropyl methylcellulose; and
   (D) about 15 to about 45 wt. % of microcrystalline cellulose.

* * * * *